United States Patent
Maji et al.

(10) Patent No.: US 10,495,866 B2
(45) Date of Patent: Dec. 3, 2019

(54) APERTURE-PLATE DRIVE MECHANISM

(71) Applicant: SHIMADZU CORPORATION, Kyoto-shi, Kyoto (JP)

(72) Inventors: Takeshi Maji, Kyoto (JP); Shunsuke Atsumi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 233 days.

(21) Appl. No.: 15/799,193

(22) Filed: Oct. 31, 2017

(65) Prior Publication Data

US 2018/0120552 A1 May 3, 2018

(30) Foreign Application Priority Data

Nov. 1, 2016 (JP) .................. 2016-214620

(51) Int. Cl.
*G02B 21/36* (2006.01)
*G02B 5/00* (2006.01)
*G01N 21/35* (2014.01)

(52) U.S. Cl.
CPC ........... *G02B 21/362* (2013.01); *G01N 21/35* (2013.01); *G02B 5/005* (2013.01); *G01N 2201/063* (2013.01)

(58) Field of Classification Search
CPC .. G02B 21/00; G02B 21/0004; G02B 21/004; G02B 21/0044; G02B 21/36; G02B 21/362; G02B 5/005; G01N 21/35; G01N 2201/063
See application file for complete search history.

(56) References Cited

U.S. PATENT DOCUMENTS 6,061,120 A * 5/2000 Nakata ............... G02B 21/0004
356/51

FOREIGN PATENT DOCUMENTS

JP 7-63994 A 3/1995
JP 2000-180726 A 6/2000

* cited by examiner

*Primary Examiner* — Stephone B Allen
*Assistant Examiner* — Adam W Booher
(74) *Attorney, Agent, or Firm* — Sughrue Mion, PLLC

(57) ABSTRACT

Provided is an aperture-plate drive mechanism including an aperture-plate open-close mechanism and a rotation mechanism for rotating the open-close mechanism. The open-close mechanism includes: drive blocks 308 fixed to a pair of aperture plates 301; a linear motion guide 306 allowing the drive blocks to move along an axis; a feed screw 302 parallel to the axis, on which a pair of helical threads proceeding in opposite directions formed; nut members 305 each of which is provided in a manner to be engaged with one of the pair of helical threads and is prevented from rotating due to a rotation of the feed screw; an urging member 309 for pressing the drive blocks onto the nut members, respectively; and a distance adjustment member 310 placed between one drive block and the corresponding nut member, for adjusting the distance between them. With this mechanism, a discrepancy between the open-close center of the aperture plates from the rotation center can be cancelled even after the mechanism is assembled.

8 Claims, 5 Drawing Sheets

APERTURE-PLATE DRIVE MECHANISM

TECHNICAL FIELD

The present invention relates to an aperture-plate drive mechanism including an open-close mechanism for opening or closing aperture plates which define the size of a measurement area on a sample in an infrared microscope or similar microscopic analyzer, as well as a rotation mechanism for rotating the aperture plates around an axis perpendicular to the aperture plates.

BACKGROUND ART

Microscopic analyzers are used for analyzing a micro-sized measurement area on a sample.

FIG. 1 shows one configuration example of an infrared microscope which is one type of the microscopic analyzer. In the infrared microscope, a sample 1 placed on a sample stage is illuminated with infrared light, and an emission of light from the illuminated area is detected with an infrared detector 9. There are two measurement methods in the infrared microscope. One method is to illuminate the sample 1 with the infrared light from the obverse side of the sample and detect the reflected light. The other method is to illuminate the sample from the reverse side of the sample 1 and detect the transmitted light.

The light emitted from the sample 1 is collected with a Cassegrain reflector 6 consisting of a concave mirror 6a with a through-hole formed at its center and a convex mirror 6b. The collected light falls onto the infrared detector 9 through a small opening (aperture 8) surrounded by a plurality of aperture plates. The aperture 8 is placed at a position which is conjugate to the sample 1 with respect to the Cassegrain reflector 6 (i.e. the position where the image of the sample 1 is formed). In a measurement, while checking the position on an image of the surface of the sample 1 taken with a camera 22, an operator drives the sample stage to locate the measurement target area at the center of the visual field of the infrared microscope. Subsequently, the operator adjusts the size of the aperture 8, and then rotates the aperture 8 to fit the visual field of the infrared microscope to the measurement target area.

The size of the aperture 8 is adjusted, for example, by opening or closing one pair of aperture plates which define the aperture width in one direction and another pair of aperture plates which define the aperture width in another direction that is perpendicular to the first direction. A feed screw (male screw) extending in the driving direction of the aperture plates is engaged with the threaded hole (female screw) formed in a drive block fixed to each aperture plate. A linear motion guide (translation bearing) determines the moving direction of the drive block while restricting the rotation of the same block. With such a mechanism, a rotation of the feed screw is converted into a linear motion of the drive block (and the aperture plate) Patent Literature 1 discloses an aperture-plate drive mechanism including an aperture-plate open-close mechanism for driving aperture plates and a rotation mechanism for rotating the aperture plates around an axis perpendicular to the aperture plates, in which each pair of the aperture plates (and drive blocks) facing each other across their open-close center are simultaneously driven in opposite directions (closer to or farther away from each other) by using, as a feed screw, a double-end screw having two helical threads proceeding in the opposite directions, with the threaded hole of one drive block engaged with each thread.

CITATION LIST

Patent Literature

Patent Literature 1: JP 2000-180726 A

SUMMARY OF INVENTION

Technical Problem

As noted earlier, an aperture-plate drive mechanism includes an aperture-plate open-close mechanism for aperture plates and a rotation mechanism. Each of the two mechanisms is constructed by assembling a plurality of members, and the entire mechanism is produced by combining the two mechanisms.

Ideally speaking, the aperture-plate drive mechanism should be manufactured so that the open-close center of each pair of the aperture plates perfectly coincides with the rotation center. Actually, a discrepancy can occur between these two centers due to some problems which occur in the manufacturing process, such as the size variation of each member or the assembling accuracy of those members. If such a discrepancy is present in the ape e-plate drive mechanism described in Patent Literature 1, a problem occurs in the measurement of a sample: After the size of the aperture is adjusted, when the aperture is rotated, the aperture becomes displaced from the measurement target area. Therefore, for every measurement of a sample, the time-consuming task of changing the position of the sample stage needs to be performed to fit the aperture to the measurement target area.

Thus, in an aperture-plate drive mechanism which includes an aperture-plate open-close mechanism for making a pair of aperture plates that defines the size of the measurement area on a sample move closer to or farther away from each other and a rotation mechanism for rotating the aperture plates around an axis perpendicular to the aperture plates, the problem to be solved by the present invention is to facilitate the task of making the open-close center and the rotation center of a pair of aperture plates coincide with each other if they are not perfectly in accordance with each other after the aperture-plate open-close mechanism and the rotation mechanism are assembled together.

Solution to Problem

The aperture-plate drive mechanism according to the present invention developed for solving the previously described problem includes:

an aperture-plate open-close mechanism including:
a) two drive blocks respectively fixed to a pair of aperture plates;
b) a linear motion guide for allowing the two drive blocks to move along an axis while preventing the drive blocks from moving in other directions;
c) a feed screw laid parallel to the axis, with a pair of helical threads proceeding in opposite directions formed on the feed screw;
d) a pair of nut members each of which is provided in a manner to be engaged with one of the pair of helical threads and is prevented from rotating due to a rotation of the feed screw;

e) an urging member for urging each of the two drive blocks in a direction parallel to the axis so as to press the two drive blocks onto the pair of nut members, respectively; and f) a distance adjustment member placed between one of the two drive blocks and the corresponding nut member, for adjusting the distance between the drive block concerned and the nut member concerned in a direction parallel to the axis; and g) a rotation mechanism for rotating the aperture-plate open-close mechanism around an axis perpendicular to the aperture plates.

In the present invention, the phrase "parallel to an axis" means that an element concerned is substantially parallel to the axis. It does not always need to be exactly parallel.

The aperture plate and the drive block may be formed as a single member, or they may be two independent members fastened together by screws or other methods.

The aperture-plate open-close mechanism may be provided with two or more pairs of aperture plates.

In the open-close mechanism included in the aperture-plate drive mechanism according to the present invention, a so-called "double-end screw", or a screw on which two helical threads proceeding in opposite directions are formed, is used as the feed screw. Each thread is engaged with the threaded hole of one nut member. Rotating the feed screw makes the two nut members move in opposite directions (closer to or farther away from each other). The urging member presses the drive blocks onto the nut members to make the drive blocks follow the motions of the n t members. As a result, the pair of aperture plates (and the drive blocks) simultaneously move in the opposite directions (closer to or farther away from each other), facing each other across their open-close center. The aperture-plate open-close mechanism further includes the distance adjustment member placed between one of the drive blocks and the corresponding nut member. This distance adjustment member allows the distance between the drive block and the nut member to be changed, whereby the open-close center of the pair of aperture plates can be shifted.

In the aperture-plate drive mechanism according to the present invention, if the open-close center of a pair of aperture plates does not coincide with the rotation center of the aperture plates, the open-close center and the rotation center can be made to coincide with each other by changing the distance between the drive block and the nut member by means of the distance adjustment member. If this adjustment is performed beforehand, the aperture will not be displaced from the measurement target area when the aperture plates are rotated after the aperture size is adjusted, so that it is unnecessary to change the position of the sample stage for each measurement of a sample.

Advantageous Effects of the Invention

By using the aperture-plate drive mechanism according to the present invention, the open-close center and the rotation center of a pair of aperture plates can be easily made to coincide with each other if they are not perfectly in accordance with each other after the drive mechanism is assembled.

DESCRIPTION OF EMBODIMENTS

Figure 1:
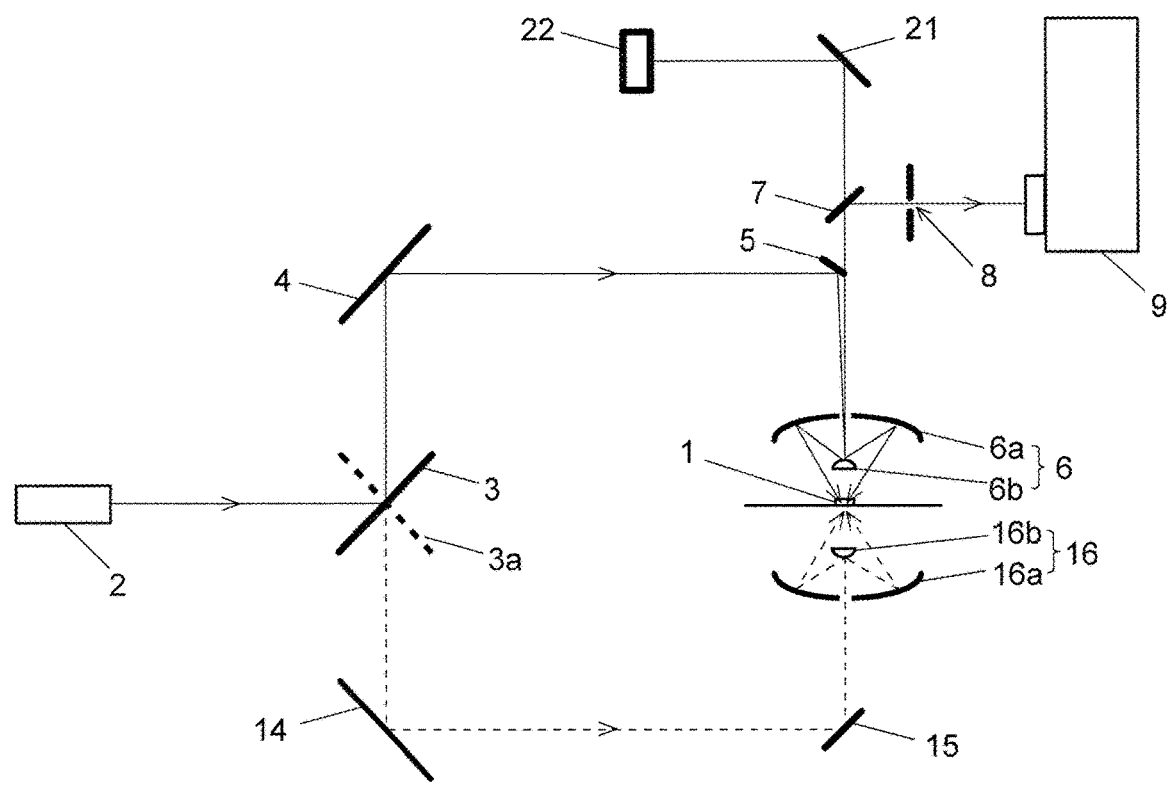
FIG. 1 is a diagram illustrating a schematic configuration of an infrared microscope.

An infrared microscope as one embodiment of a microscopic analyzer including an aperture-plate drive mechanism according to the present invention is hereinafter described with reference to the drawings.

The configuration of the infrared microscope in the present embodiment is similar to the one described earlier with reference to FIG. 1. The configuration is once more described with reference to the same figure. The infrared microscope in the present embodiment is capable of detecting either transmitted or reflected light from a sample 1 placed on a sample stage (not shown).

In the case of detecting reflected light from the sample 1, a beam of infrared light whose intensity temporally changes (interferogram) is generated by a light source unit 2 including an interferometer of a Fourier transform infrared spectrophotometer (FTIR). This light is sequentially reflected by a first mirror 3, second mirror 4 and third mirror 5. Then, the light passes through the hole formed at the center of the concave mirror 6a of the Cassegrain reflector 6 and falls onto the convex mirror 6b of the same reflector. Subsequently, the light is collected by the concave mirror 6a and cast onto the sample 1.

The reflected light from the sample 1 is collected by the concave mirror 6a and the convex mirror 6b (Cassegrain reflector 6). After being reflected by a mirror which reflects only infrared light ("hot mirror") 7, the light passes through an aperture 8 and is eventually detected by an infrared detector 9. A focusing optical system (not shown; e.g. Cassegrain reflector or concave mirror) for focusing the light from the aperture 8 onto the light-receiving surface of the infrared detector 9 is appropriately placed between the aperture 8 and the infrared detector 9. The aperture 8 and the light-receiving surface of the infrared detector 9 are each placed at a position which is conjugate to the sample 1 (a position at which an image of the sample is formed). By Fourier-transforming the detection signals produced by the infrared detector 9, a spectrum is obtained.

In the case of detecting transmitted light from the sample 1, the first mirror 3 is rotated by 90 degrees (the first mirror 3a indicated by the broken line in FIG. 1). The light emitted from the light source unit 2 is sequentially reflected by the first mirror 3a, fourth mirror 14 and fifth mirror 15. Then, the light passes through the hole formed at the center of the concave mirror 16a of a Cassegrain reflector 16 and falls onto the convex mirror 16b of the same reflector. Subsequently, the light is collected by the concave mirror 16a and cast onto the sample 1. The light transmitted through the sample 1 is collected by the concave mirror 6a and the convex mirror 6b. After being reflected by the hot mirror 7, the light passes through the aperture 8 and is eventually detected by the infrared detector 9.

A visible-light mirror 21 provided above the sample 1 and a camera 22 are used for allowing operators to visually check the state of the surface of the sample 1 illuminated with visible light cast from a visible-light source (not show).

Figure 2:
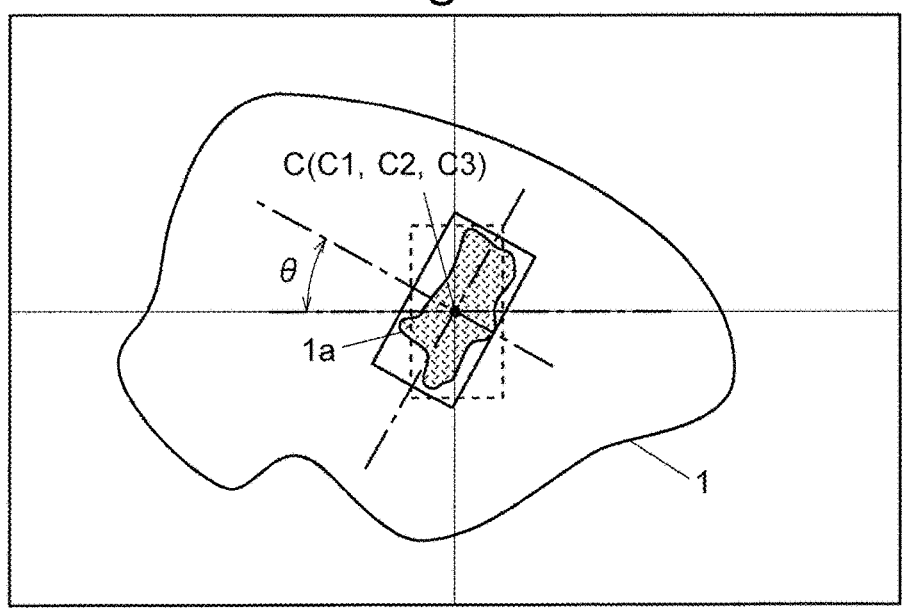
FIG. 2 is a diagram illustrating the process of determining a measurement target area on a sample in one embodiment of the present invention.

In a measurement of the sample 1, the user determines the measurement target area 1a on the surface of the sample 1 (FIG. 2) while checking the visible image of the surface of the sample 1 taken with the camera 22. Subsequently, by operating the aperture-plate drive mechanism (which will be described later), the user adjusts the size and angle of the aperture 8 so that only the infrared light from the measurement target area 1a enters the infrared microscope.

The configuration of the aperture-plate drive mechanism used for adjusting the size and angle of the aperture 8 in the infrared microscope according to the present embodiment is hereinafter described with reference to FIGS. 3-7 as well as in comparison with the conventional configuration.

Figure 3:
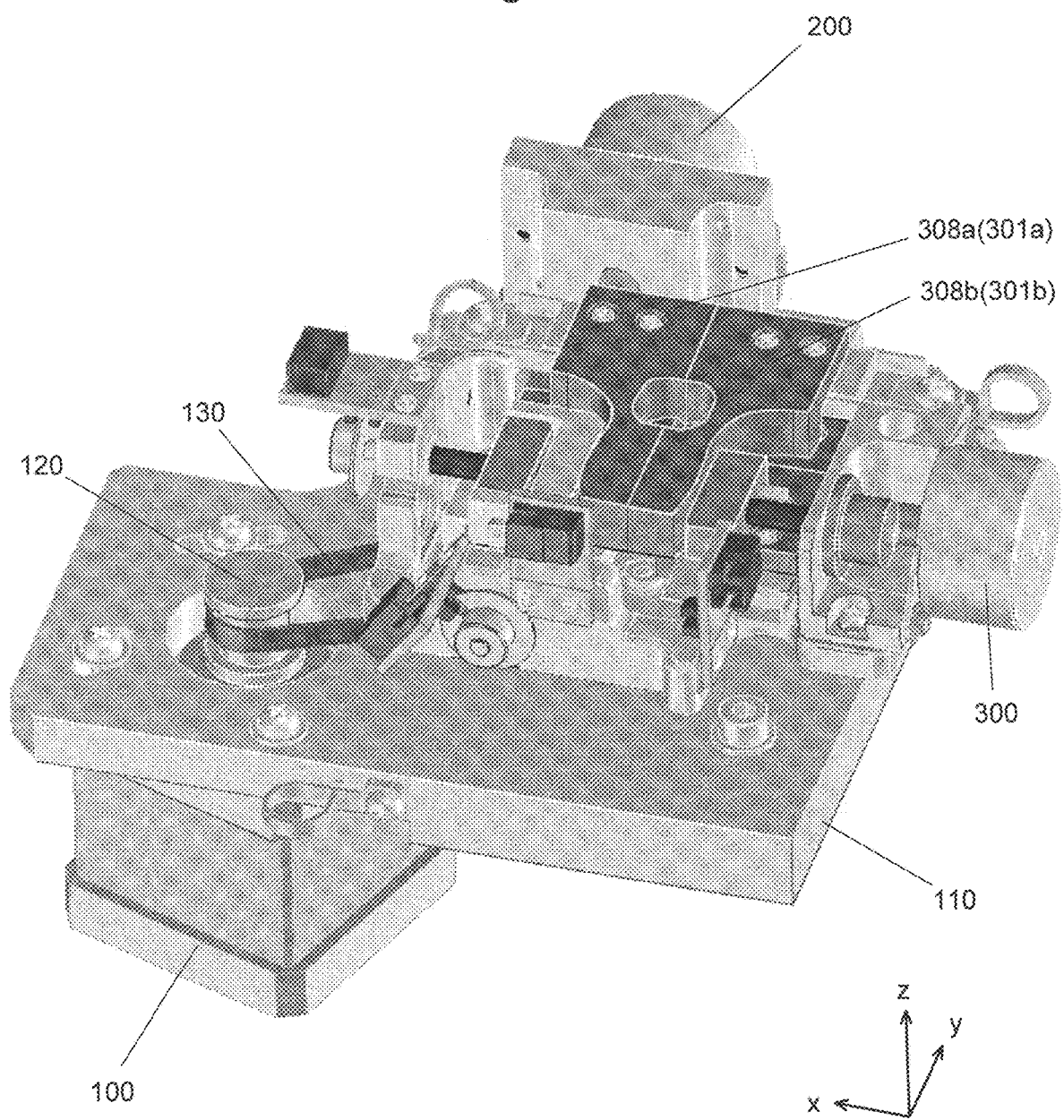
FIG. 3 is an external view of the aperture-plate drive mechanism included in an infrared microscope according to the present embodiment.

FIG. 3 is an external view of the aperture-plate drive mechanism in the present embodiment. There are two pairs of aperture plates; one pair is driven to open and close in the x-direction, while the other pair is driven in the v-direction. The aperture plates 301a and 301b driven in the x-direction are located above the ones driven in the y-direction. The aperture-plate drive mechanism in the present embodiment is roughly composed of the aperture-plate open-close mechanism for adjusting the size of the aperture 8 and the aperture-plate rotation mechanism for adjusting the angle of the aperture 8. The aperture-plate drive mechanism in the present embodiment is particularly characterized by the aperture-plate open-close mechanism.

The aperture-plate open-close mechanism is provided for each of the two directions which are orthogonal to each other (which are called the "x-direction" and "y-direction") These mechanisms are mounted in layers on an x-y stage 110 included in the aperture-plate rotation mechanism. The aperture-plate rotation mechanism includes a motor 100, rotation axis member 120, and hollow shaft 140 in addition to the x-y stage 110. When the motor 100 is energized, the rotation axis member 120 rotates. Its rotation is transmitted to the hollow shaft 140 via a belt 130. The hollow shaft 140 has a through-hole formed at its center (i.e. at the position corresponding to the aperture 8). The shaft is also connected to the x-y stage 110. The rotation of the hollow shaft 140 produces a rotation of the x-y stage 110 in the x-y plane. The motor 300 shown in the drawings is the drive source for rotating a teed screw (which will be described later) in the open-close mechanism for the aperture plates 301a and 301b in the x-direction. Similarly, the motor 200 functions as the drive source in the open-close mechanism for the aperture plates in the y-direction.

Figure 4:
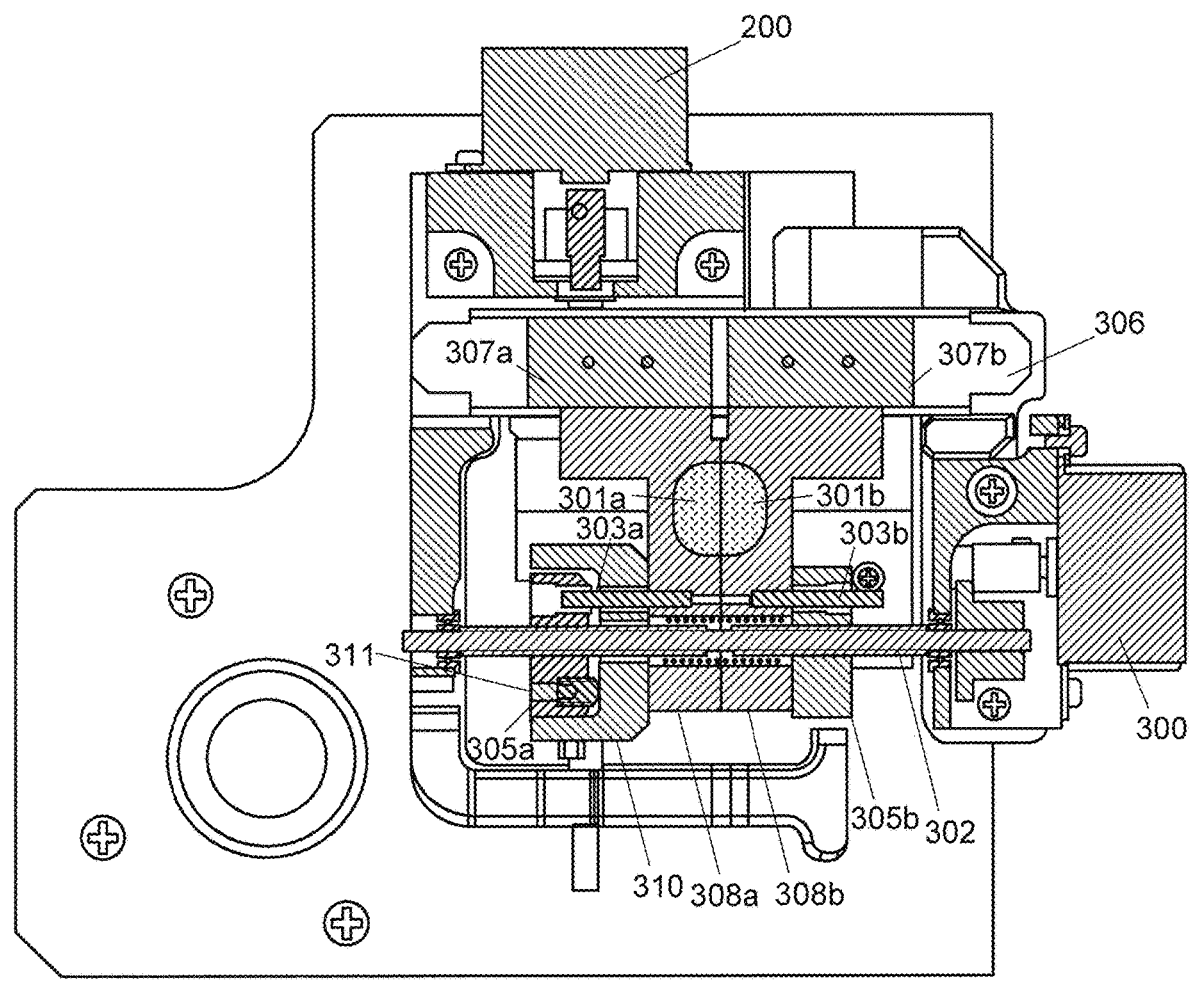
FIG. 4 is a sectional view illustrating a schematic configuration of the aperture-plate open-close mechanism included in the infrared microscope according to the present embodiment.
Figure 5:
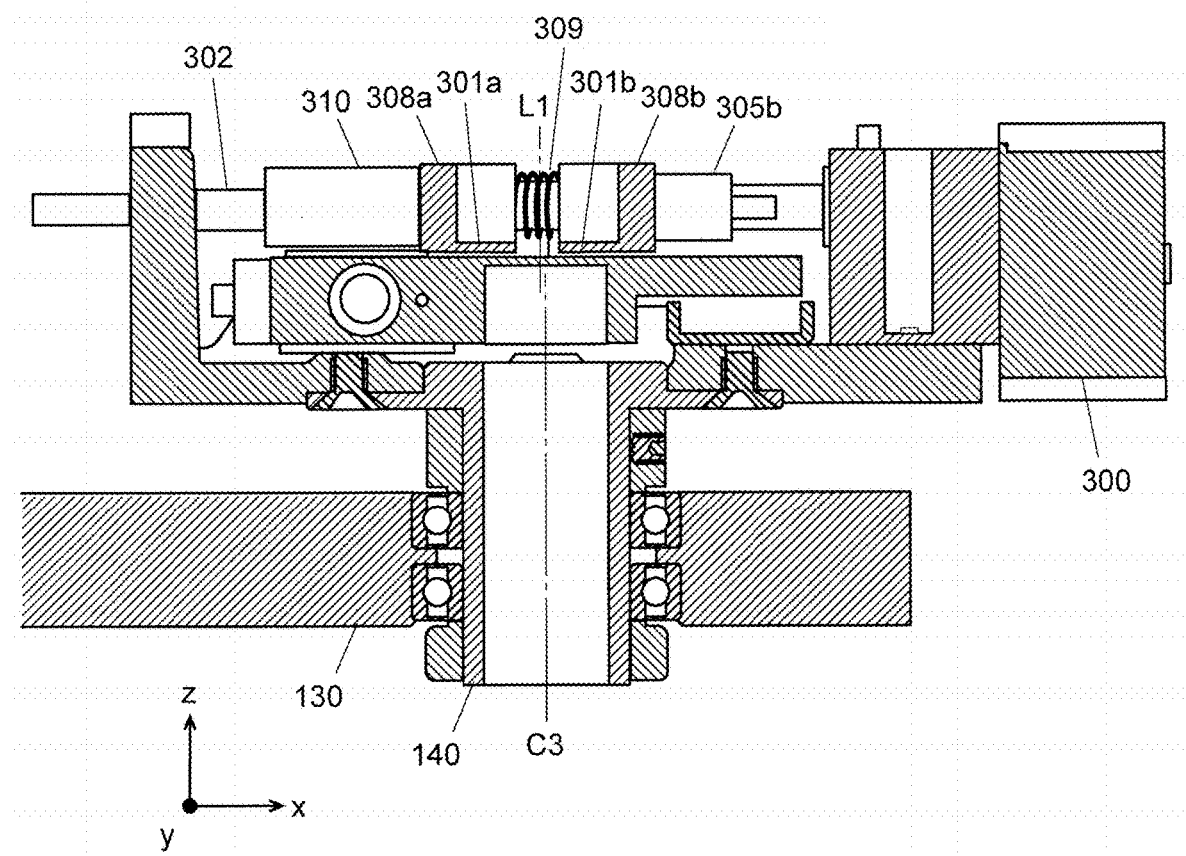
FIG. 5 is a vertical sectional view of a portion of the aperture-plate open-close mechanism included in the infrared microscope according to the present embodiment.
Figure 6:
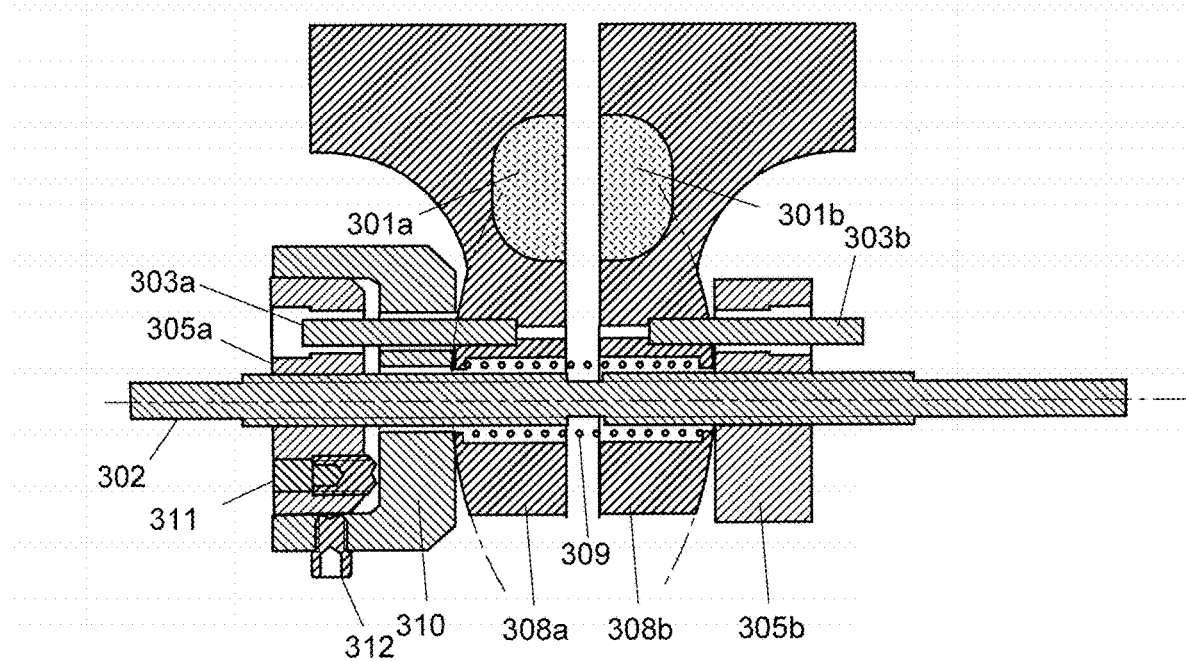
FIG. 6 is an enlarged view of a portion of the aperture-plate open-close mechanism included in the infrared microscope according to the present embodiment.
Figure 7:
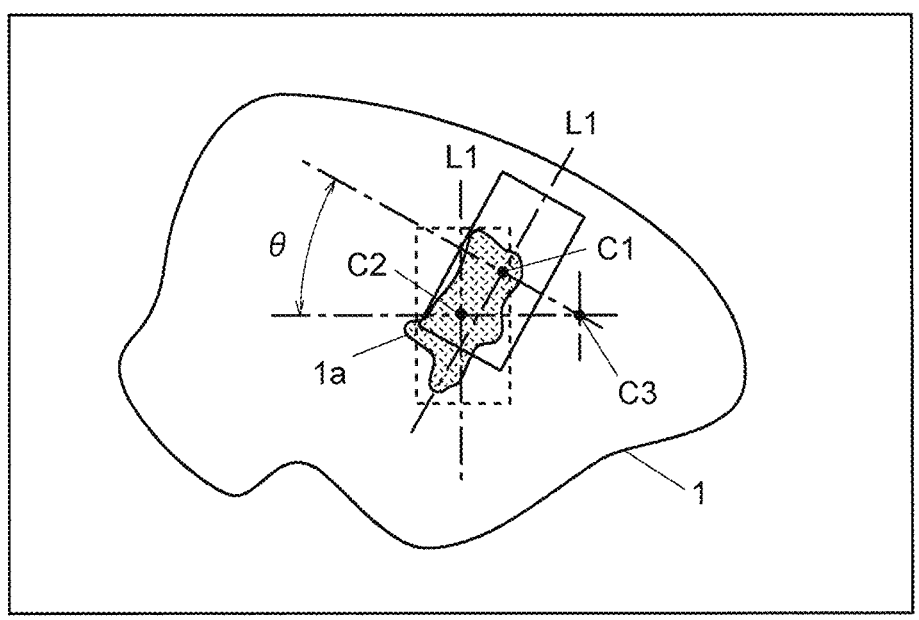
FIG. 7 is a diagram illustrating the problem which arises if the center of the aperture does not coincide with the rotation center in an aperture-plate drive mechanism included in a conventional infrared microscope.

FIG. 4 is a sectional view showing a schematic configuration of the open-close mechanism for the aperture plates 301a and 301b. A portion of this figure is presented as a transparent view for ease of understanding of the configuration of the individual components. FIG. 5 is a vertical sectional view of a portion of the open-close mechanism for the aperture plates 301a and 301b. FIG. 6 is an enlarged view of a portion of the open-close mechanism for the aperture plates 301a and 301b. The two aperture-plate open-close mechanisms respectively provided for the x-direction and y-direction are identical in configuration (except that they are arranged in mutually orthogonal directions). Therefore, the following description only deals with the detailed configuration of the open-close mechanism for the aperture plates 301a and 301b in the x-direction.

The aperture plates 301a and 301b are provided as a portion of the drive blocks 308a and 308b. The drive blocks 308a and 308b are respectively connected to guide members 307a and 307b which can move only in a specific direction ("along an axis") on a guide rail 306 of a linear motion guide. Each combination of the drive block and guide member moves as a single unit. The drive blocks 308a and 308b are respectively provided with insertion pins 303a and 303b which are to be inserted into the through-holes of float nuts 305a and 305b (which will be described later). The blocks also have through-holes into which a feed screw 302 and a spring 309 (both of which will be described later) are to be inserted. The aperture plates 301a and 301b (drive blocks 308a and 308b) constitute one pair. By moving these plates closer to or farther away from each other, the width of the aperture 8 in the x-direction is adjusted.

This open-close mechanism for the apertures 301a and 301b has a feed screw 302 laid along the x-direction on which two oppositely-directed threads are formed from the central portion toward both ends. Float nuts 305a and 305b are respectively engaged with those oppositely-directed threads. The float nuts 305a and 305b each have a through-hole in addition to the threaded hole (female screw). The aforementioned insertion pins 303a and 303b are inserted into these through-holes. These pins prevent the float nuts 305a and 305b from rotating due to the rotation of the feed screw 302. Consequently, a rotation of the feed screw 302 produces a linear motion of the float nuts 305a and 305b in the opposite directions along the x-direction. The float nut 305a also has another threaded hole which is different from the one engaged with the feed screw 302. The threaded hole is engaged with an adjusting screw 311 (which will be described later).

The two drive blocks 308a and 308b are located at a central portion of this feed screw 302. The float nut 305a is placed on the outside of the drive block 308a via an adjusting holder 310 (which will be described later), while the float nut 305b is placed on the outside of the drive block 308b.

Into the through-holes formed in the two drive blocks 308 and 308b, the feed screw 302 is inserted, along with a spring 309 for urging the drive blocks 308a and 308b toward the float nuts 305a and 305b placed on their respective outsides.

The surface of the drive block 308a in contact with the adjusting holder 310 and the surface of the drive block 308b in contact with the float nut 305b are each shaped like a convex surface (cylindrical surface) having a curvature in the y-direction, as indicated by the alternate long and short dashed lines in FIG. 6. The contact surfaces of the adjusting holder 310 and the float nut 305b are flat surfaces. Accordingly, the drive blocks 308a and 308b each have a line contact with the adjusting holder 310 and the float nut 305b in the z-direction.

In the open-close mechanism for the aperture plates 301a and 301b according to the present embodiment, the threaded holes are formed in the float nuts 305 and 305b. Those holes are engaged with the feed screw 302. The float nuts 305a and 305b are driven by the rotation of the feed screw 302. The spring 309 presses the drive blocks 308a and 308b onto the float nuts 305a and 305b, respectively, so as to make the drive blocks 308a and 308b follow the movement of the float nuts 305a and 305b. The surfaces of the drive blocks 308a and 308*b* in contact with the flat surfaces of the adjusting holder 310 and the float nut 305*b* are curved. Therefore, even if the extending direction of the guide rail 306 which restricts the moving direction of the drive blocks 308*a* and 308*b* (via the guide members 307*a* and 307*b*) is not perfectly parallel to the axis of the feed screw 302, the drive blocks 308*a* and 308*b* come in contact with the adjusting holder 310 and the float nut 305*b* at positions corresponding to the angle made by the two aforementioned directions, thereby allowing for the discrepancy. Furthermore, the drive blocks 308*a* and 308*b* are slidable on the flat surfaces of the adjusting holder 310 and the float nut 305*b*. Therefore, even if the separation distance between the guide rail 306 and the feed screw 302 is different from the design distance, the drive blocks 308*a* and 308*b* come in contact with the adjusting holder 310 and the float nut 305*b* at positions corresponding to that difference, thereby allowing for the difference. In this manner, the feed screw 302 is prevented from coining in Unbalanced contact with the inside of the threaded holes of the float nuts 305*a* and 305*b*, so that the drive blocks 308*a* and 308*b* as well as the aperture plates 301*a* and 301*b* connected to these blocks can be accurately driven over a long period of time.

The distance adjustment section included in the aperture-plate drive mechanism in the present embodiment is hereinafter described, along with a description of a problem in a conventional aperture-plate drive mechanism.

An aperture-plate drive mechanism includes an aperture-plate open-close mechanism in each of the x and y directions as well as a rotation mechanism. Each of the two types of mechanisms is constructed by assembling a plurality of members, and the entire mechanism is produced by combining those mechanisms.

Ideally speaking, the aperture-plate drive mechanism should be manufactured so that the open-close center L1 of each pair of the aperture plates perfectly coincides with the rotation center C3. Actually, a discrepancy can occur between these two centers due to some problems which occur in the manufacturing process, such as the size variation of each member or the assembling accuracy of those members. Such a situation is hereinafter described with reference to FIG. 7.

As described earlier, the process of fitting the aperture to the measurement target area is as follows: Initially, the aperture plates are driven in each of the x and y directions to adjust the aperture to a size which corresponds to that of the measurement target area 1*a*. In this operation, the center C1 of the aperture is also made to coincide with the center C2 of the measurement target area.

Subsequently, the aperture-plate rotation mechanism is operated to rotate the aperture plates around an axis perpendicular to the aperture plates by angle θ. As noted earlier, in the present example, the open-close center L1 of the aperture plates is displaced from the rotation center C3 of the aperture plates. Therefore, when the aperture-plate open-close mechanism is rotated around this rotation center C3, the aperture is dislocated from the measurement target area 1*a*. Therefore, it has conventionally been necessary to change the position of the sample stage to cancel this discrepancy.

In the aperture-plate drive mechanism according to the present embodiment, the adjusting holder 310 is located between the drive block 308*a* and the float nut 305*a*. This adjusting holder 310 is a member having a U-shaped section whose two sides at both ends are slidably fitted on the side surface of the float nut 305*a*. An adjusting screw 311 is fitted in the threaded hole formed in the float nut 305*a* The tip of this screw 311 is in contact with the surface corresponding to the central side of the aforementioned U-shape in the adjusting holder 310. By driving this screw forward or backward, the separation distance between the float nut 305*a* and the surface corresponding to the central side of the U-shape in the adjusting holder 310 can be adjusted. Accordingly, by adjusting the position of the adjusting screw 311, the distance between the float nut 305*a* and the drive block 308*a* can be adjusted via the adjusting holder 310. Subsequently, the adjusting holder 310 is fixed on the float nut 305*a* so as to maintain the adjusted distance. In the present embodiment, this fixation is achieved by inserting a fixing screw 312 into a threaded hole formed in the side wall of the adjusting holder 310 until the tip of this screw comes in firm contact with the side surface of the float nut 305*a*.

The aperture-plate drive mechanism in the present embodiment is also produced similarly to the conventional one; i.e. the open-close mechanism and the rotation mechanism are each constructed by assembling a plurality of members, and the entire mechanism is produced by combining those mechanisms. Therefore, at the completion of production, the open-close center L1 of the aperture plates 301*a* and 301*b* does not always coincide with their rotation center C3. However, in the present embodiment, if the open-close center L1 of the aperture plates 301*a* and 301*b* is displaced from the rotation center C3, the displacement can be eliminated by appropriately changing the distance between the float nut 305*a* and the drive block 308*a* in the previously described manner to adjust the position of the adjusting holder 310 so that the open-close center L1 of the aperture plates 301*a* and 301*b* coincides with the rotation center C3. By performing this adjustment in each of the aperture-plate open-close mechanisms for the x and y directions, the center of the aperture 8 can be made to coincide with the rotation center C3. It is preferable to perform this process before the completed aperture-plate drive mechanism is shipped.

The previously described embodiment is a mere example and can be appropriately changed within the spirit of the present invention.

The previous embodiment is concerned with a drive mechanism provided with an open-close mechanism for each of the x and y directions. In the case of performing a measurement on a slit-like measurement target area, the open-close mechanism only needs to be provided for one of the two directions.

In the previous embodiment, the distance adjustment section including the adjusting holder 310 and other parts is only provided between the drive block 308*a* and the float nut 305*a*. A similar distance adjustment section may also be provided between the drive block 308*b* and the float nut 305*b*.

The distance adjustment section in the previous embodiment includes the adjusting holder 310, adjusting screw 311 and fixing screw 312. Actually, the distance adjustment section may be embodied in various specific forms as long as it allows for the adjustment and fixation of the distance between the drive block 308*a* and the float nut 305*a*. For example, a plurality of adjusting holders with different thicknesses may be prepared from which an appropriate one can be selectively placed between the drive block 308*a* and the float nut 305*a*. As another example, two plate members having a variable separation distance may be placed between the drive block 308*a* and the float nut 305*a*.

In the previous embodiment, the nut members are arranged on the outside of the drive blocks. Their positional relationship may be reversed. In that case, the spring should be arranged so as to press each drive block from outside inward (toward the nut member).

In the previous embodiment, the rotation of the nut members due to the rotation of the feed screw is prevented by the pins inserted into the through-holes formed in the nut members. The rotation may also be prevented by a member arranged on the outside of the nut members.

REFERENCE SIGNS LIST

1 . . . Sample
1a . . . Measurement Target Area
2 . . . Light Source Unit
3, 3a . . . First Mirror
4 . . . Second Mirror
5 . . . Third Mirror
6, 16 . . . Cassegrain Reflector
6a, 16a . . . Concave Mirror
6b, 16b . . . Convex Mirror
8 . . . Aperture
9 . . . Infrared Detector
14 . . . Fourth Mirror
15 . . . Fifth Mirror
21 . . . Visible-Light Mirror
22 . . . Camera
100 . . . Motor
110 . . . x-y Stage
120 . . . Rotation Axis Member
130 . . . Belt
140 . . . Hollow Shaft
200, 300 . . . Motor
301a, 301b . . . Aperture Plate
303a, 303b . . . Insertion Pin
305a, 305b . . . Float Nut
306 . . . Guide Rail
307a, 307b . . . Guide Member
308a, 308b . . . Drive Block
309 . . . Spring
310 . . . Adjusting Holder
311 . . . Adjusting Screw
312 . . . Fixing Screw

The invention claimed is:

1. An aperture-plate drive mechanism, comprising:
an aperture-plate open-close mechanism including:
   a) two drive blocks respectively fixed to a pair of aperture plates;
   b) a linear motion guide for allowing the two drive blocks to move along an axis while preventing the drive blocks from moving in other directions;
   c) a feed screw laid parallel to the axis, with a pair of helical threads proceeding in opposite directions formed on the feed screw;
   d) a pair of nut members each of which is provided in a manner to be engaged with one of the pair of helical threads and is prevented from rotating due to a rotation of the feed screw;
   e) an urging member for urging each of the two drive blocks in a direction parallel to the axis so as to press the two drive blocks onto the pair of nut members, respectively; and
   f) a distance adjustment member placed between one of the two drive blocks and the corresponding nut member, for adjusting a distance between the drive block concerned and the nut member concerned in a direction parallel to the axis;
   and
   g) a rotation mechanism for rotating the aperture-plate open-close mechanism around an axis perpendicular to the aperture plates.

2. The aperture-plate drive mechanism according to claim 1, wherein the open-close mechanism is provided for each of two non-parallel directions.

3. The aperture-plate drive mechanism according to claim 1, wherein:
a contact portion of each of the drive blocks being in contact with one of the nut members or the distance adjustment member along the axis has a convex surface, while a contact portion of a corresponding element has either a flat surface or a concave surface having a larger radius of curvature than the convex surface.

4. The aperture-plate drive mechanism according to claim 1, wherein:
a contact portion of each of the nut members or the distance adjustment member being in contact with one of the drive blocks along the axis has a convex surface, while a contact portion of the drive block concerned has either a flat surface or a concave surface having a larger radius of curvature than the convex surface.

5. An infrared microscope including an aperture-plate drive mechanism, comprising:
an aperture-plate open-close mechanism including:
   a) two drive blocks respectively fixed to a pair of aperture plates;
   b) a linear motion guide for allowing the two drive blocks to move along an axis while preventing the drive blocks from moving in other directions;
   c) a feed screw laid parallel to the axis, with a pair of helical threads proceeding in opposite directions formed on the feed screw;
   d) a pair of nut members each of which is provided in a manner to be engaged with one of the pair of helical threads and is prevented from rotating due to a rotation of the feed screw;
   e) an urging member for urging each of the two drive blocks in a direction parallel to the axis so as to press the two drive blocks onto the pair of nut members, respectively, and
   f) a distance adjustment member placed between one of the drive blocks and the corresponding nut member, for adjusting a distance between the drive block concerned and the nut member concerned in a direction parallel to the axis;
   and
   g) a rotation mechanism for rotating the aperture-plate open-close mechanism around an axis perpendicular to the aperture plates.

6. The infrared microscope according to claim 5, wherein the open-close mechanism is provided for each of two non-parallel directions.

7. The infrared microscope according to claim 5, wherein:
a contact portion of each of the drive blocks being in contact with one of the nut members or the distance adjustment member along the axis has a convex surface, while a contact portion of a corresponding element has either a flat surface or a concave surface having a larger radius of curvature than the convex surface.

8. The infrared microscope according to claim 5, wherein:
a contact portion of each of the nut members or the distance adjustment member being in contact with one of the drive blocks along the axis has a convex surface, while a contact portion of the drive block concerned has either a flat surface or a concave surface having a larger radius of curvature than the convex surface.

* * * * *